(12) United States Patent
Doeberitz et al.

(10) Patent No.: US 8,946,171 B2
(45) Date of Patent: Feb. 3, 2015

(54) IMMUNIZATION OF AN INDIVIDUAL AGAINST CARCINOMAS AND THE PRELIMINARY STAGES THEREOF

(76) Inventors: Magnus Von Knebel Doeberitz, Heidelberg (DE); Michael Linnebacher, Stennweiler (DE); Wolfgang Rudy, Bretten (DE)

( * ) Notice: Subject to any disclaimer, the term of this patent is extended or adjusted under 35 U.S.C. 154(b) by 417 days.

(21) Appl. No.: 12/500,458

(22) Filed: Jul. 9, 2009

(65) Prior Publication Data

US 2011/0064770 A1    Mar. 17, 2011

Related U.S. Application Data

(60) Division of application No. 11/433,386, filed on May 15, 2006, now Pat. No. 7,569,538, which is a continuation of application No. 10/203,206, filed as application No. PCT/DE01/00470 on Feb. 7, 2001, now abandoned.

(30) Foreign Application Priority Data

Feb. 10, 2000 (DE) .................................. 100 06 033

(51) Int. Cl.
*A61K 48/00* (2006.01)
*A61K 38/08* (2006.01)
*A61K 39/00* (2006.01)

(52) U.S. Cl.
CPC ......... *A61K 39/0011* (2013.01); *A61K 2039/53* (2013.01)
USPC ..................... 514/44 R; 424/277.1; 514/19.2; 514/19.3

(58) Field of Classification Search
None
See application file for complete search history.

(56) References Cited

U.S. PATENT DOCUMENTS

| | | | |
|---|---|---|---|
| 5,733,920 A | 3/1998 | Mansuri et al. | |
| 6,709,832 B1 * | 3/2004 | Von Knebel Doeberitz et al. | 435/7.23 |

FOREIGN PATENT DOCUMENTS

| | | | |
|---|---|---|---|
| DE | 198 29 473 | | 1/2000 |
| WO | WO 98/45444 | | 10/1998 |
| WO | WO 99/02183 | | 1/1999 |
| WO | WO 99/19357 | | 4/1999 |
| WO | WO00/01845 | * | 1/2000 |

OTHER PUBLICATIONS

Tuting et al (Cancer Gene therapy, 1999, vol. 6, pp. 73-80).*
Trisha Gura, "Systems for Identifying New Drugs Are Often Fault", Science, vol. 278, pp. 1041-1042, Nov. 7, 1997.
Matteo Bellone et al., "Cancer Immunotherapy: Syntheitc and Natural Peptides in the Balance", Immunology Today, vol. 20, No. 10, pp. 457-461, Oct. 1999.
Alexander Gaiger et al., "Immunity to WT 1 in the Animal Model and in Patients with Acute Myeloid Leukemia", Blood, vol. 6, No. 4, pp. 1480-1489, Aug. 15, 2000.
R. Ian Freshney, "Culture of Animal Cells", A Manual of Basic Technique, Alan R. Liss, Inc., New York, p. 4, 1983.
Gerald B. Dermer, "Another Anniversary for the War on Cancer", Bio/Technology, vol. 12, pp. 320, Mar. 1994.
J.H. Carter et al., "Cycling—An Overexpressed Cell Cycle Protein as a Potential Tumour Antigen Target for Immunotherapy", Immunology, vol. 95, No. Suppl. 1, pp. 104, Dec. 1998.

* cited by examiner

*Primary Examiner* — Karen Canella
(74) *Attorney, Agent, or Firm* — Crowell & Moring LLP

(57) ABSTRACT

The present invention relates to a pharmaceutical composition, comprising a cell cycle regulatory protein and/or an expressible nucleic acid coding for this in an amount suitable for immunization of an individual against carcinomas and the preliminary stages thereof and common auxiliary agents and/or to the use of a cell cycle regulatory protein and/or an expressible nucleic acid coding for this to immunize an individual against carcinomas and the preliminary stages thereof.

4 Claims, No Drawings

SEQUENCE LISTING

```
<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Val Met Met Met Gly Ser Ala Arg Val
1               5

<210> SEQ ID NO 2
<211> LENGTH: 9
<212> TYPE: PRT
<213> ORGANISM: Homo sapiens
```

```
<400> SEQUENCE: 2

Val Leu His Arg Ala Gly Ala Arg Leu
1               5

<210> SEQ ID NO 3
<211> LENGTH: 9
<212> TYPE: PRT
<213> ORGANISM: Homo sapiens

<400> SEQUENCE: 3

Thr Leu Thr Arg Pro Val His Asp Ala
1               5

<210> SEQ ID NO 4
<211> LENGTH: 9
<212> TYPE: PRT
<213> ORGANISM: Homo sapiens

<400> SEQUENCE: 4

Leu Leu His Gly Ala Glu Pro Asn Cys
1               5

<210> SEQ ID NO 5
<211> LENGTH: 9
<212> TYPE: PRT
<213> ORGANISM: Homo sapiens

<400> SEQUENCE: 5

Ser Met Glu Pro Ser Ala Asp Met Leu
1               5

<210> SEQ ID NO 6
<211> LENGTH: 10
<212> TYPE: PRT
<213> ORGANISM: Homo sapiens

<400> SEQUENCE: 6

Met Met Gly Ser Ala Arg Val Ala Glu Leu
1               5                   10

<210> SEQ ID NO 7
<211> LENGTH: 10
<212> TYPE: PRT
<213> ORGANISM: Homo sapiens

<400> SEQUENCE: 7

Leu Leu Leu His Gly Ala Glu Pro Asn Cys
1               5                   10

<210> SEQ ID NO 8
<211> LENGTH: 10
<212> TYPE: PRT
<213> ORGANISM: Homo sapiens

<400> SEQUENCE: 8

Gly Val Met Met Met Gly Ser Ala Arg Val
1               5                   10
```

IMMUNIZATION OF AN INDIVIDUAL AGAINST CARCINOMAS AND THE PRELIMINARY STAGES THEREOF

This is a divisional of application Ser. No. 11/433,386, filed May 15, 2006 now U.S. Pat. No. 7,569,538 which is a continuation of application Ser. No. 10/203,206, filed Dec. 23, 2002 now abandoned, which is a 371 application of International Application No. PCT/DE01/00470, filed Feb. 7, 2001, which claims priority to DE 100 06 033.1, filed Feb. 10, 2000, all of which are incorporated herein by reference.

The present invention relates to a pharmaceutical composition containing a cell cycle regulatory protein and to the use of the pharmaceutical composition for immunizing an individual against carcinomas and the preliminary stages thereof.

Several million people fall ill with, and die of, carcinomas world-wide every year. These mortality rates have remained unchanged for many years despite intensive therapy research. Until now, patients suffering from carcinomas often have to undergo carcinoma-removing surgery or chemotherapy or radiation therapy. However, this is accompanied by very massive side-effects which then contribute to the mortality rates of patients suffering from carcinomas.

It is thus the object of the present invention to provide a product by means of which therapeutic and prophylactic steps can be taken against carcinomas, the above side-effects being avoided.

According to the invention this is achieved by the subject matters defined in the claims.

The present invention is based on Applicant's findings that in carcinomas or the preliminary stages thereof cell cycle regulatory proteins are available in modified form or amount. For example, overexpression of cyclin-dependent kinase inhibitors is found in carcinomas (cf. Applicant's German patent 198 29 473). Applicant also found out that individuals can be immunized against cell cycle regulatory proteins modified as regards form or amount so as to take therapeutic and prophylactic steps against carcinomas and the preliminary stages thereof. Applicant showed this by way of in vitro and in vivo experiments (cf. below example).

The present invention thus relates to a pharmaceutical composition, comprising a cell cycle regulatory protein and/or an expressible nucleic acid coding for this in an amount suitable for immunization of an individual against carcinomas and the preliminary stages thereof as well as common auxiliary agents.

The employed term "cell cycle regulatory protein" comprises cell cycle regulatory proteins of any kind and origin. For example, these may be cyclins. In particular, these may be cyclin-dependent kinases, such as cdk4 and cdk6, which regulate the cyclins. More particularly, these may be cyclin-dependent kinase inhibitors which, in turn, regulate the cyclin-dependent kinases. Examples of cyclin-dependent kinase inhibitors are the proteins p15, p16, p18, p19, with p16 being preferred. The cell cycle regulatory proteins may be available in wild-type or modified form. The latter form comprises modifications of the amino acid sequence, such as additions, deletions, substitutions and/or inversions of one or more amino acids. Fragments of cell cycle regulatory proteins as such or in combination with carriers may also be present, the fragments being able to have a wild-type or modified amino acid sequence. It is favorable for the carriers in the individual not to be immunogenic. Such carriers may be the individual's own proteins or foreign proteins or fragments thereof. Carriers, such as serum albumin, fibrinogen or transferrin or a fragment thereof are preferred. It is particularly favorable for the fragments of the cell cycle regulatory proteins to contain epitopes which are recognized by cytotoxic T cells, e.g. $CD8^+$ T cells, and may induce a cytotoxic immune response. Such epitopes of cell cycle regulatory proteins can be determined by methods with which a person skilled in the art is familiar, in particular by using an NIH software system available on the NIH bioinformation service website. It can also be advantageous for different cell cycle regulatory proteins or fragment thereof, to which the above explanations apply correspondingly, to be simultaneously present. For the production of the above cell cycle regulatory proteins, reference is made e.g. to Sambrook et al., Molecular Cloning: A Laboratory Manual, 2nd edition, Cold Spring Harbor Laboratory Press, Cold Spring Harbor N.Y. (1989).

The employed term "expressible nucleic acid coding for a cell cycle regulatory protein" comprises any nucleic acid, e.g. RNA or DNA, expressible in an individual and coding for a cell cycle regulatory protein, to which the above explanations apply correspondingly. The nucleic acid can be present as such, i.e. together with elements suitable for the expression thereof, or in combination with a vector. Examples of such elements are promoters and enhancers, such as CMV, SV40, RSV metallothionein I and polyhedrin promoter or CMV and SV40 enhancers. Further sequences suitable for expression are disclosed in Goeddel: Gene Expression Technology: Methods in Enzymology 185, Academic Press, San Diego, Calif. (1990). Moreover, any vectors suitable for expression in mammalian cells can be used as vectors. These are e.g. pcDNA3, pMSX, pKCR, pEFBOS, cDM8 and pCEV4 as well as vectors derived from pcDNAI/amp, pcDNAI/neo, pRc/CMV, pSV2gpt, pSV2neo, pSV2-dhfr, pTk2, pRSVneo, pMSG, pSVT7, pko-neo and pHyg. Recombinant viruses, e.g. adenovirus, vaccinia virus or adeno-associated virus, can also be used as vectors. As regards the production of the above nucleic acids, in particular vectors containing such nucleic acids, reference is made to Sambrook et al., supra, for example.

The employed term "carcinomas and the preliminary stages thereof" comprises carcinomas of any kind and origin and preliminary stages thereof. For example, these may be carcinomas of the upper respiratory tract or anogenital carcinomas, in particular the cervical carcinoma and the preliminary stages thereof, such as cervical intraepithelial neoplasia (CIN carcinoma in situ (CIS), etc. Likewise benign modifications such as papillomas, adenomas, hyperplasias or similar proliferations of epithelial, mesenchymal or hematopoietic proliferations are also to be counted thereamong.

The employed term "individual" comprises an individual of any kind and origin having cell cycle regulatory proteins and being able to fall ill with carcinomas and/or their preliminary stages. Examples of such individuals are humans and animals as well as cells thereof.

The employed term "amount suitable for immunization of an individual" comprises any amount of a cell cycle regulatory protein, to which the above explanations apply correspondingly, or an expressible nucleic acid coding for this, to which the above explanations apply correspondingly, and with which an individual can be immunized. The amount depends on whether a cell cycle regulatory protein or an expressible nucleic acid coding for this is used. The amount also depends on whether immunization of the individual rather aims at an induction of antibodies directed against modified cell cycle regulatory proteins or a stimulation of cytotoxic T cells, e.g. $CD8^+$ T cells, directed against modified cell cycle regulatory proteins. Both possibilities of immunization can be achieved by the present invention. Furthermore, the amount depends on whether immunization is intended as a prophylactic or therapeutic treatment. In addition, the individual's age, sex and weight play a role for determining the amount. It is favorable to give the individual 100 μg-1 g of a cell cycle regulatory protein or $10^6$-$10^{12}$ MOI of a recombinant virus containing an expressible nucleic acid coding for a cell cycle regulatory protein by means of injection. The injection may be made at various sites of the individual intramuscularly, subcutaneously, intradermally or in any other form of application. It may also be favorable to carry out one or more "booster injections" having about equal amount. In this case, it may be particularly favorable to use different fragments of the respective cell cycle regulatory proteins for the individual injections.

The employed term "common auxiliary agents" comprises any auxiliary agents suitable for a pharmaceutical composition to immunize an individual. Such auxiliary agents are e.g. immunization adjuvants, such as GM-CSF or Freund's adjuvant, buffered common salt solutions, water, emulsions, such as oil/water emulsions, wetting agents, sterile solutions, etc.

By means of the present invention it is possible to immunize individuals, in particular humans and animals, against modified cell cycle regulatory proteins. Immunization takes place by both induction of antibodies and stimulation of $CD8^+$ T cells, directed against modified cell cycle regulatory proteins. Thus, it is possible to take prophylactic and therapeutic steps against carcinomas and the preliminary stages thereof.

The invention is explained by the below example.

EXAMPLE

Stimulation of CDS+ T Cells Against the Cyclin-Dependent Kinase Inhibitor p16 and Lysis of p16-Overexpressing Carcinoma Cells (A) Stimulation of CDS+ T Cells Against p16

Peripheral mononuclear cells are obtained from a healthy donor and subjected to what is called ELISPOT analysis. It is the principle of this experiment to stimulate lymphocytes in culture vessels with specific antigens. Whenever the lymphocytes are activated as they recognize the antigen, the activated lymphocytes release cytokines which, in turn, bind to specific antibodies immobilized on the bottom surface of the culture vessels. Having washed out the lymphocytes, the bound cytokines can be detected in the culture vessels by means of a second antibody made visible in a subsequent color reaction.

Peripheral blood lymphocytes (PBL) from an HLA-A0201-positive healthy proband are purified by density centrifugation via a Ficoll Paque® gradient. T-lymphocytes are obtained by separating the B-lymphocytes or the monocytes using antibody-coupled magnetobeads (CD 11, CD 16, CD 19, CD36 and CD56) (Pant T cell isolation Kit®, Milteny, Bergisch Gladbach, Germany). About $2 \times 10^7$ T cells are obtained from 30 ml blood.

HLA-A0201-restricted peptides of p16 are identified by means of an NIH software system (available on the NIH bioinformation service). These are the below peptides: TABLE-US-00001 9mer peptides: 10mer peptides: score 1: VMMMGSARV (SEQ ID NO: 1) score 1: MMGSARVAEL (SEQ ID NO: 6) score 2: VLHRAGARL (SEQ ID NO: 2) score 2: LLLHGAEPNC (SEQ ID NO: 7) score 3: TLTRPVHDA (SEQ ID NO: 3) score 3: GVMMMGSARV (SEQ ID NO: 8) score 4: LLHGAEPNC (SEQ ID NO: 4) score 5: SMEPSADML (SEQ ID NO: 5)

The isolated T cells are incubated with T2 cells, which (a) have been loaded with a mixture of the above 9mer peptides (10 μg/peptide) and (b) with a mixture of the above 10mer peptides (10 μg/peptide). The T cells are restimulated once a week for a period of 6 weeks. $10^7$ T cells each are cocultured with $2 \times 10^6$ peptide-loaded T2 cells in 24-well plates.

The reactivity over the peptide-loaded T2 cells is determined once a week, starting on day 0 of the experiment, by carrying out IFNI-γ elispot analysis. On day 28, a reactivity is observed by the mixture of (a) (400 specific cells per million cells). The main reactivity is in this case directed against the peptide VMMMGSARV (SEQ ID NO: 1) (1,000 specific cells/1,000,000 cells). A less intensive activity is observed against the mixture of (b) (150 specific cells/1,000,000 cells). Here, the peptide MMGSARVAEL (SEQ ID NO: 6) shows maximum reactivity (600 specific cells/1,000,000 cells).

Hence it is evident that it is possible to stimulate $CD8^+$ T cells activated against p16.

(B) Lysis of p16-Overexpressing Carcinoma Cells

Following another restimulation, the activated $CD8^+$ T cells are incubated with the HLA A0201+ cervical carcinoma cells Caski, which overexpress p16. The colon carcinoma cells SW480 which do not overexpress p16 are used as controls. $10^6$ Caski cells are labeled with $^{52}Cr$ (100 μCi) at 37° C. for 1 h and cocultured with increasing numbers of activated CD8+ T cells or 3 hours. Specific lysis of the Caski cells is determined by the amount of released radioactivity in the supernatant.

It turns out that Caski cells are lyzed by the activating $CD8^+$ T cells but not by the control cells SW480.

The invention claimed is:

1. A method for immunizing against carcinomas and the preliminary stages thereof, comprising use of an expressible nucleic acid coding for the cyclin-dependent kinase inhibitor p16 or fragments thereof, wherein the carcinomas are those of the upper respiratory tract and/or anogenital carcinomas;

and wherein the fragment or fragments contain epitopes which can be detected by cytotoxic T cells and elicit a cytotoxic immune response.

2. The method of claim 1, wherein the anogenital carcinoma is a cervical carcinoma.

3. The method according to claim 1, wherein the expressible nucleic acid codes for a wild-type form of protein p16.

4. The method according to claim 1, wherein the fragment comprises the amino acid sequence of SEQ ID NO: 1 or SEQ ID NO: 6.

* * * * *